(12) United States Patent
Xu et al.

(10) Patent No.: US 9,345,835 B2
(45) Date of Patent: May 24, 2016

(54) CARTRIDGE STOPPER FOR AN INTRADERMAL DELIVERY SYSTEM

(75) Inventors: Ying Xu, Parsippany, NJ (US); Robert Banik, Long Valley, NJ (US); Lionel Vedrine, Palo Alto, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 531 days.

(21) Appl. No.: 12/737,453

(22) PCT Filed: Jul. 17, 2009

(86) PCT No.: PCT/US2009/004131
§ 371 (c)(1),
(2), (4) Date: May 3, 2011

(87) PCT Pub. No.: WO2010/008574
PCT Pub. Date: Jan. 21, 2010

(65) Prior Publication Data
US 2011/0213311 A1    Sep. 1, 2011

Related U.S. Application Data

(60) Provisional application No. 61/082,041, filed on Jul. 18, 2008.

(51) Int. Cl.
*A61M 5/00* (2006.01)
*A61M 5/315* (2006.01)
*A61M 5/24* (2006.01)

(52) U.S. Cl.
CPC ....... *A61M 5/31511* (2013.01); *A61M 5/31515* (2013.01); *A61M 5/31573* (2013.01);

(Continued)

(58) Field of Classification Search
CPC .............. A61M 5/31511; A61M 5/24; A61M 5/31551; A61M 5/31585; A61M 5/31573; A61M 5/2466; A61M 2005/2407
USPC .......................... 604/195, 228, 311, 232, 218
See application file for complete search history.

(56) References Cited

U.S. PATENT DOCUMENTS 4,391,272 A * 7/1983 Staempfil ...................... 604/110
4,421,508 A   12/1983 Cohen
(Continued)

FOREIGN PATENT DOCUMENTS

JP      54-129793 A    10/1979
JP      11-502731 A     3/1999
(Continued)

OTHER PUBLICATIONS

Notice of Rejection dated Jul. 30, 2013 issued by the Japanese Patent Office in counterpart Japanese application No. 2011-518735.
(Continued)

*Primary Examiner* — Edelmira Bosques
(74) *Attorney, Agent, or Firm* — Dickinson Wright PLLC

(57) ABSTRACT

A device for delivering a medicament intradermally includes a cartridge (112) having a first end (110) and a second end (114) and defining a volume (111) therebetween. The volume (111) is adapted to contain the medicament. A driving member (121) has a first end (126) and a second end (128). The first end (126) of the driving member (121) is disposed in the cartridge (112) and the second end (128) of the driving member (121) is disposed outside the cartridge (112). A stopper (115) is slidably disposed in the cartridge volume (111). The driving member (121) is releasably disposed in the stopper (115) such that when the driving member (121) is retracted from the cartridge (112) the stopper (115) is disengaged from the driving member (121) and remains in the cartridge volume (111).

17 Claims, 19 Drawing Sheets

(52) U.S. Cl.
CPC ............... *A61M 5/24* (2013.01); *A61M 5/2466* (2013.01); *A61M 5/31551* (2013.01); *A61M 5/31585* (2013.01); *A61M 2005/2407* (2013.01)

(56) References Cited

U.S. PATENT DOCUMENTS

| | | | |
|---|---|---|---|
| 4,677,980 A * | 7/1987 | Reilly et al. | 600/432 |
| 4,701,165 A * | 10/1987 | DeHaitre | 604/228 |
| 4,931,040 A * | 6/1990 | Haber et al. | 604/110 |
| 4,931,043 A * | 6/1990 | Ray et al. | 604/228 |
| 4,955,870 A | 9/1990 | Ridderheim et al. | |
| 4,973,318 A * | 11/1990 | Holm et al. | 604/208 |
| 5,141,495 A * | 8/1992 | Olovson | 604/110 |
| 5,308,331 A * | 5/1994 | Avila et al. | 604/110 |
| 5,378,240 A * | 1/1995 | Curie et al. | 604/110 |
| 5,697,915 A * | 12/1997 | Lynn | 604/191 |
| 6,004,300 A * | 12/1999 | Butcher et al. | 604/222 |
| 2002/0016573 A1 | 2/2002 | Munk | |
| 2004/0127858 A1 * | 7/2004 | Bendek et al. | 604/208 |
| 2006/0178631 A1 | 8/2006 | Gillespie et al. | |
| 2006/0229562 A1 | 10/2006 | Marsh et al. | |

FOREIGN PATENT DOCUMENTS

| | | |
|---|---|---|
| JP | 2000-342688 A | 12/2000 |
| JP | 2003-522608 A | 7/2003 |
| JP | 2004-500904 A | 1/2004 |
| JP | 2004-527361 A | 9/2004 |
| JP | 2008-522751 A | 7/2008 |
| WO | 95/17915 A2 | 7/1995 |
| WO | 9629106 A2 | 9/1996 |
| WO | 00/32259 A2 | 6/2000 |
| WO | 0110484 A1 | 2/2001 |
| WO | 01/60434 A1 | 8/2001 |
| WO | 02098470 A1 | 12/2002 |
| WO | 2004/093940 A2 | 11/2004 |
| WO | 2005/099793 A1 | 10/2005 |
| WO | 2006063124 A2 | 6/2006 |
| WO | 2008/020023 A1 | 2/2008 |
| WO | 2008/064283 A2 | 5/2008 |

OTHER PUBLICATIONS

Reexamination Report Issued in Japanese Patent Application No. 2011-518735 dated Oct. 15, 2014.

* cited by examiner

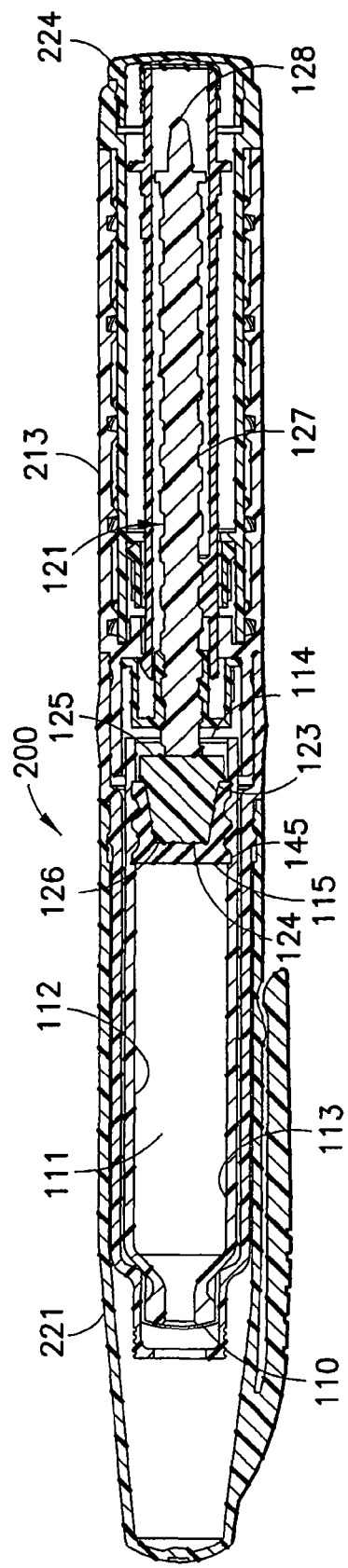
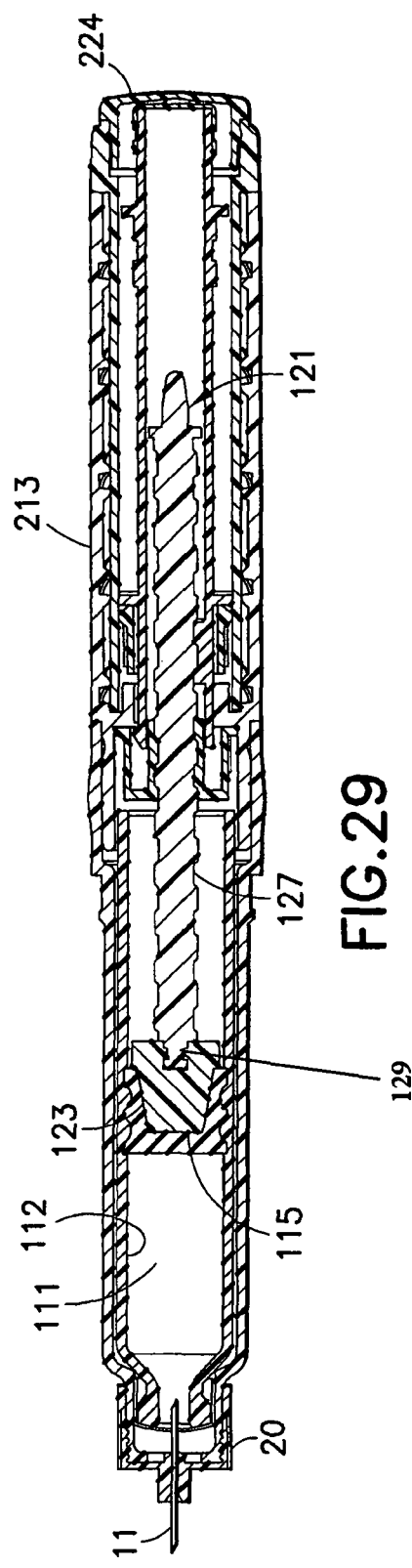
FIG.28
FIG.29

CARTRIDGE STOPPER FOR AN INTRADERMAL DELIVERY SYSTEM

CROSS REFERENCE TO RELATED APPLICATION

This application claims the benefit under 35 U.S.C. §119(e) of provisional application Ser. No. 61/082,041, filed Jul. 18, 2008, the entire disclosure of which is hereby incorporated by reference.

FIELD OF THE INVENTION

The present invention relates to a cartridge stopper used in an intradermal delivery system. More particularly, the present invention relates to a cartridge stopper that releasably receives a driving member, thereby improving dose accuracy and reducing "drooling" of the medicament.

BACKGROUND OF THE INVENTION

In certain circumstances, it is desirable to inject medication directly into human tissue. Typically, syringes are used to inject medicaments into tissue areas, such as the intramuscular tissue layer, the subcutaneous tissue layer, and the intradermal tissue layer. Each of these tissue layers has specific characteristics that affect the amount of fluid pressure needed to inject a fluid into the targeted tissue layer. When injecting fluids into each of these tissue layers, the user must exert enough force on the injection device to overcome different amounts of backpressure associated with the particular tissue layer. In general, practitioners and self-injectors, such as diabetics, are familiar with the force necessary to inject fluids into the subcutaneous layer. Injections into the subcutaneous and intramuscular tissue layers can cause discomfort to the patient or self-injector because of the characteristics of the tissue, needle length and needle diameter or gauge. It is desirable to employ shorter, smaller gauge needles to achieve delivery into the intradermal tissue layer.

It is noted that when the needle lengths are shortened and needle diameters are made smaller, the fluid dynamics of the injection device changes. Additionally, the fluid dynamics between the injection device and the targeted tissue layer also change because the shorter needle length injects the fluid into a different tissue layer, such as the intradermal layer. Because the tissue density between the intramuscular, subcutaneous, and intradermal tissue layers varies, the ease with which fluid may be injected into each type of tissue layer varies. The variation in tissue density causes changes in the backpressure exerted by the tissue against the fluid when it is injected. For instance, the backpressure associated with the intradermal tissue layer is greater than the backpressure associated with the subcutaneous tissue layer.

Currently, several pen injection systems are commercially available for subcutaneous substance delivery of medication. These pen injection systems typically use 29 to 31 gauge needles having lengths of between 5 mm and 12.7 mm, and are used to deliver the contents of a medicament cartridge, such as insulin, to the subcutaneous tissue layers of a patient rapidly and conveniently. The medicament cartridges are generally of a standard volume and size (including a fixed cross sectional area). The pressure of delivery is the quotient of the actuation force exerted by a user and the cross sectional area of the cartridge. Because the cross-sectional area of the cartridge is fixed, higher delivery pressures require higher actuation forces by the user.

A "microneedle" pen system has been developed that reduces the pain and sensation to the user normally experienced with subcutaneous substance delivery. Such "microneedle" drug delivery systems may include shorter needles, typically less than or equal to 3 mm, with smaller diameters, in the range of 30 to 34 gauge or thinner. Such needle length and gauge size combinations are desirable to provide for sharp, yet short, point geometries that can more accurately target substance delivery to only certain selected tissue, such as the deep intradermal or shallow subcutaneous tissue layers, thereby permitting controlled fluid delivery. Current typical pen injection systems used for subcutaneous delivery are not believed optimal for use by the general population of self-injectors for delivery into the intradermal layer because of, inter alia, the high backpressures associated with injecting fluid into the intradermal layers of the skin using microneedles.

To achieve effective medication delivery to the targeted tissue layer in light of higher backpressures, it is desirable to control two factors: the depth accuracy of the injection and the rate of the injection. This is of particular interest in connection with intradermal injections because the backpressures are relatively high, but similar analysis can be applied when injecting into the intramuscular or the subcutaneous tissue layers. The delivery of medicament within the narrow depth range of the intradermal tissue layer should first be assured, and maintained during injection. Once the depth accuracy is obtained, the rate of injection should be controlled to minimize or eliminate leakage of the medicament into other tissue layers or back out through the skin. Additional details of intradermal drug delivery and microneedles have been previously described in U.S. Pat. No. 6,494,865, issued on Dec. 17, 2002, U.S. Pat. No. 6,569,143, issued on May 27, 2003, PCT Publication No. WO 2005/025461, published on Mar. 24, 2005, and U.S. Patent Application Publication No. 2005/0065472, published on Mar. 24, 2005, all of which are assigned to Becton, Dickinson and Company, and the entire content of each such patent and application being incorporated herein by reference.

The intradermal tissue layer of the skin is considerably denser than the subcutaneous tissue region. The density of the intradermal tissue layer on a particular patient is, in part, a function of the patient's collagen make-up, which is affected by the patient's age, and the location of the injection site on the patient's body. This increased density of the intradermal tissue layer can create a greater backpressure resistance on the injection device than the resistance created when injecting into the subcutaneous tissue region. To overcome the increased backpressure resistance when injecting into the intradermal tissue layer with a conventional pen system, the user or patient would need to exert greater actuation force (which could be substantial) on the injector device actuator or employ some sort of powered injector device. In these applications, the injector device must be designed to withstand the greater backpressure from the intradermal injection site as well as the additional force exerted by the user or patient. Further, the increased actuation force required to actuate the injector device may result in the fluid "jetting" past the desired tissue depth due to the increased fluid pressure.

Conventional pen-type injection systems may require that the user keep the needle seated in the skin for a period of up to about 10 seconds, after the injection has been completed, to allow for the "axial compliance" of the pen mechanism (or lead screw) and the cartridge back-end stopper to equilibrate to minimize "drool" from the needle tip upon withdrawal.

Such time periods may need to be increased to accommodate any additional axial compliance resulting from higher back-pressures.

As described above, the back pressure is high for intradermal delivery. This high pressure poses a challenge for dose accuracy, which is important for certain drug therapy, such as insulin. One of the resulting problems is the compressibility of the cartridge stopper, which is contributes to dose inaccuracy. Existing devices overcome this problem by adding a hard core inside the cartridge stopper. However, this solution results in manufacturing problems. Additionally, as shown in FIGS. 3 and 4, the conventional stopper 15 is generally a solid member made of a rubber material. An end of the lead screw 7 abuts an end of stopper 15 within the cartridge 2. However, axial displacement of the lead screw 7 and stopper 15 during dose delivery results in high compression of the stopper 15, thereby resulting in inaccurate doses.

Accordingly, a need exists for an intradermal delivery system that improves dose accuracy and minimizes medicament "drooling".

SUMMARY OF THE INVENTION

In accordance with an aspect of the present invention, a stopper allows a driving member to nest inside the stopper as the hard core to increase the effective hardness of the cartridge stopper.

The stopper according to an exemplary embodiment of the present invention reduces deformation in cartridges, syringes and other equivalent delivery systems that encounter high pressures, such as back pressures, from intradermal injections, from the use of a thin needle gage, from the injection of viscous liquid, or from a high speed injection. The shape of the stopper allows the delivery device driving mechanism to mate inside the stopper, thereby giving the stopper support while also allowing the plunger to be "self-centering" because of the tapered walls. By reducing the height (thickness) of the soft rubber in the cartridge and replacing it with the rigid plastic plunger tip, the volume compression is reduced without changing materials. This allows the stopper according to an exemplary embodiment of the present invention to be made of currently approved stopper materials that are validated for long-term insulin contact.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which:

FIG. 28 is an elevational view in cross section of a drug delivery pen having a stopper and driving member according to an exemplary embodiment of the present invention;

FIG. 29 is an elevational view in cross section of the drug delivery pen of FIG. 28 in which the cap is removed and the needle hub;

Throughout the drawings, like reference numbers will be understood to refer to like parts, components and structures.

DETAILED DESCRIPTION OF THE EXEMPLARY EMBODIMENTS

Figure 1:
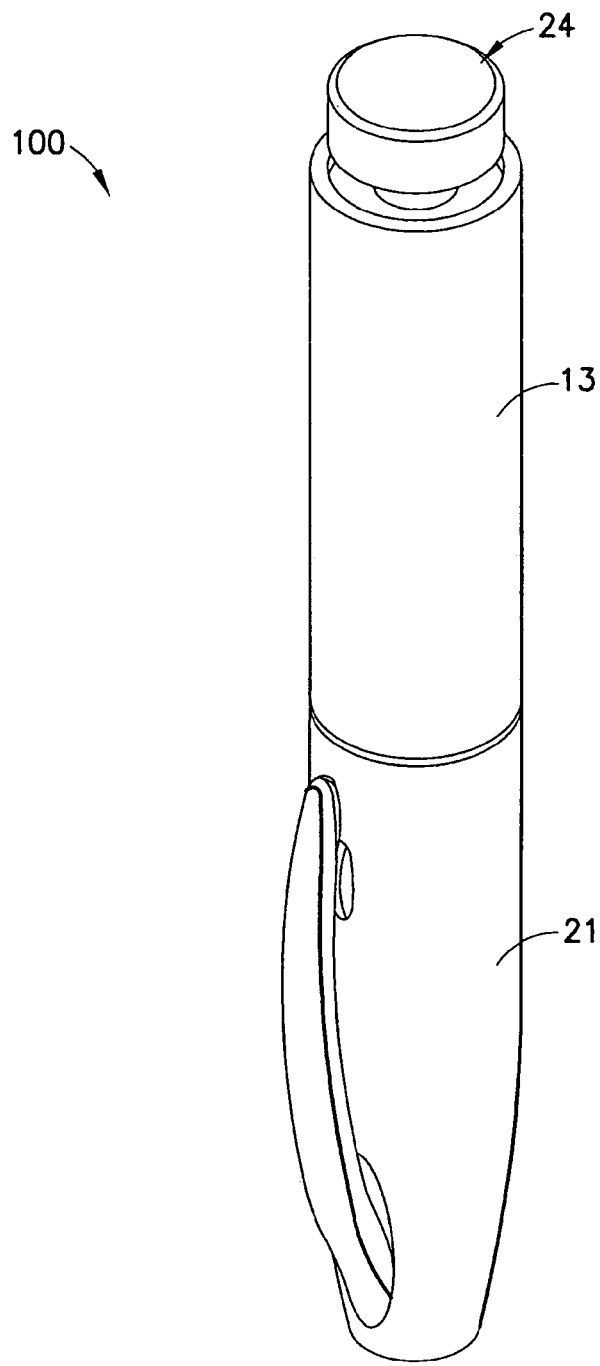
FIG. 1 is a perspective view of an assembled existing pen injector assembly.
Figure 2:
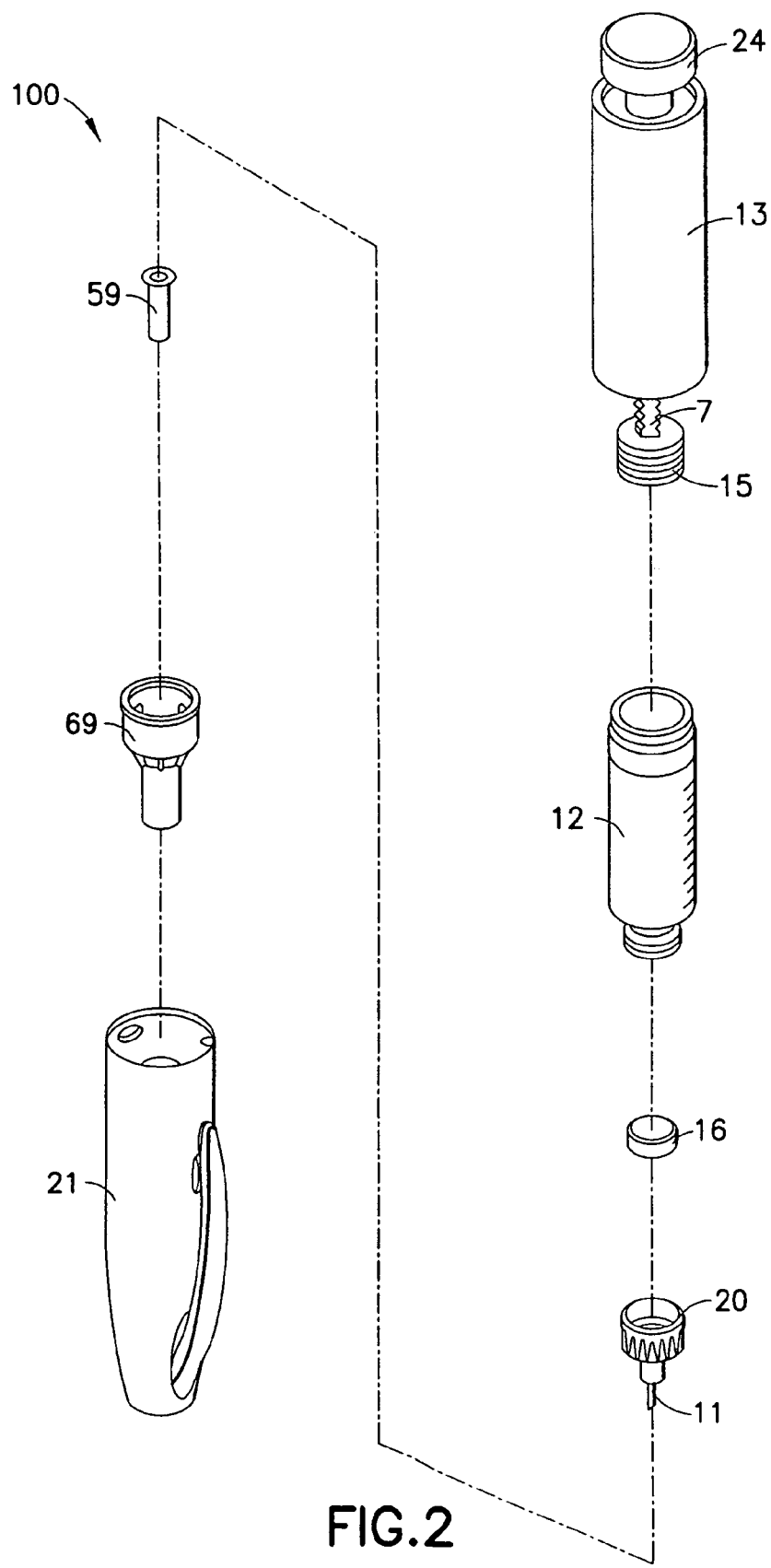
FIG. 2 is an exploded perspective view of the components of the pen needle assembly of FIG. 1.

The following description and details of exemplary embodiments of the present invention, while generally disclosed in a typical drug delivery pen as shown in FIGS. 1 and 2, could more broadly apply to a needle and hub assembly for use in conjunction with, or incorporated onto, other injection devices such as syringes and infusion devices. The assembly and operation of a typical drug delivery pen, as shown in FIGS. 1 and 2, is described in U.S. patent application Ser. No. 11/102,874, which is hereby incorporated by reference in its entirety.

Pen injector devices, such as the exemplary drug delivery pen 100, as shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the drug delivery pen 100 in a shirt pocket, purse or other suitable location.

Figure 3:
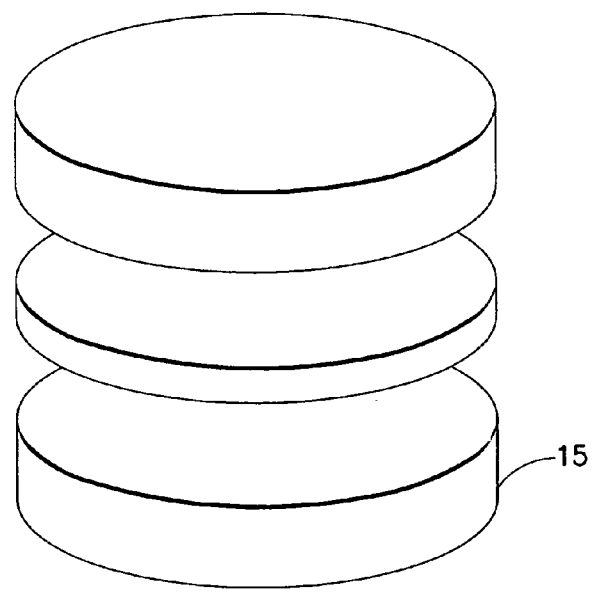
FIG. 3 is a perspective view of an existing stopper for the pen needle assembly of FIGS. 1 and 2.
Figure 4:
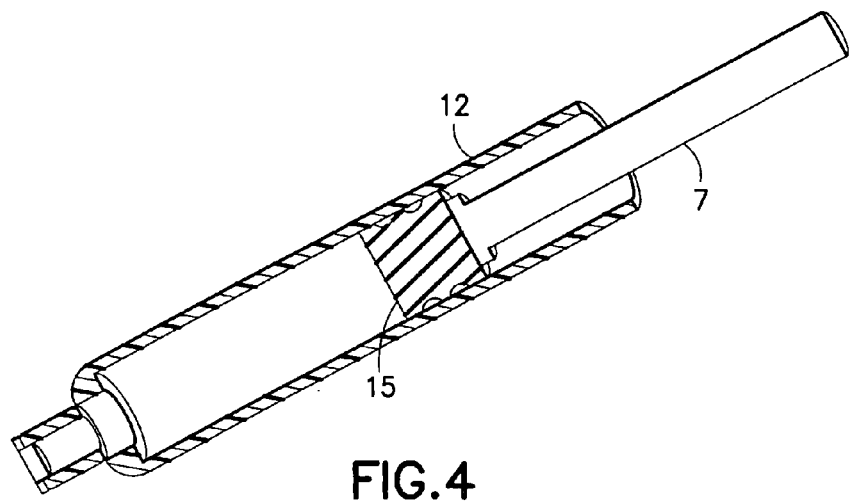
FIG. 4 is a perspective view in cross section of the stopper of FIG. 3 disposed within a cartridge of the pen needle assembly of FIGS. 1 and 2.

FIG. 2 is an exploded view of an exemplary drug delivery pen shown in FIG. 1. The dose knob/button 24 has a dual purpose and is used to both set the dosage of the medication to be injected and used to inject the dosed medicament via the lead screw 7 and stopper 15 (FIG. 3) through the medicament cartridge 12 attached to the invention through the hub or reservoir housing 20. In standard drug delivery pens, the dosing and delivery mechanisms are all found within the outer sleeve 13 and are not described in greater detail here as they are understood by those knowledgeable of the prior art. The medicament cartridge 12 is typically attached to a standard pen injector housing via known attachment means, such as ¼ turn fastening features. The distal movement of the plunger or stopper 15 within the medicament cartridge 12, as shown in FIG. 4, causes medication to be forced into the reservoir housing 20. The medicament cartridge 12 is sealed by septum 16, which is punctured by a septum penetrating needle cannula (not shown) located within reservoir housing 20. Reservoir housing 20 is preferably screwed onto the medicament cartridge 12, although other attachment means can be used. To protect a user, or anyone who handles the pen injection device 100, an outer shield 69, which attaches to the reservoir housing 20, covers the reservoir housing. An inner shield 59 covers the patient needle 11 within the outer shield 69. The inner shield 59 can be secured to the reservoir housing 20 to cover the patient needle 11 by any suitable means, such as an interference fit or a snap-fit. The outer shield 69 and inner shield 59 are removed prior to use. The cap 21 fits snugly against outer sleeve 13 to allow a user to securely carry the drug delivery pen 100.

Figure 5:
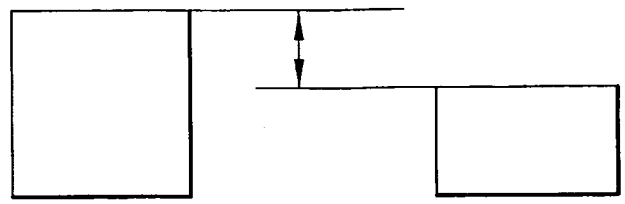
FIG. 5 is an illustration of the compression of the stopper of FIG. 3.

The medicament cartridge 12 is typically a glass tube sealed at one end with the septum 16 and sealed at the other end with the stopper 15. The septum 16 is pierceable by a septum penetrating cannula (not shown), but does not move with respect to the medicament cartridge 12. The stopper 15 is axially displaceable within the medicament cartridge 12 while maintaining a fluid tight seal. As shown in FIGS. 3 and 4, an existing stopper 15 has a solid, planar top surface against which an end of the lead screw 7 abuts. However, such a configuration of the stopper 15 and lead screw 7 results in high compression of the stopper, as shown in FIG. 5, thereby resulting in inaccurate doses and "drooling" from the needle 11.

An exemplary embodiment of the present invention is shown in FIGS. 6-14 and 28-30. The cartridge 112 is shown in FIGS. 7, 13 and 28-30. A volume 111 is defined between a first end 110 and a second end 114 and is adapted to receive a medicament. The septum 16 (FIG. 2) is disposed at the first end 110 of the cartridge 112, and the stopper 115 is disposed proximal the second end 114 of the cartridge, thereby sealing the volume 111. The cartridge 112 has an inner surface 113.

Figure 7:
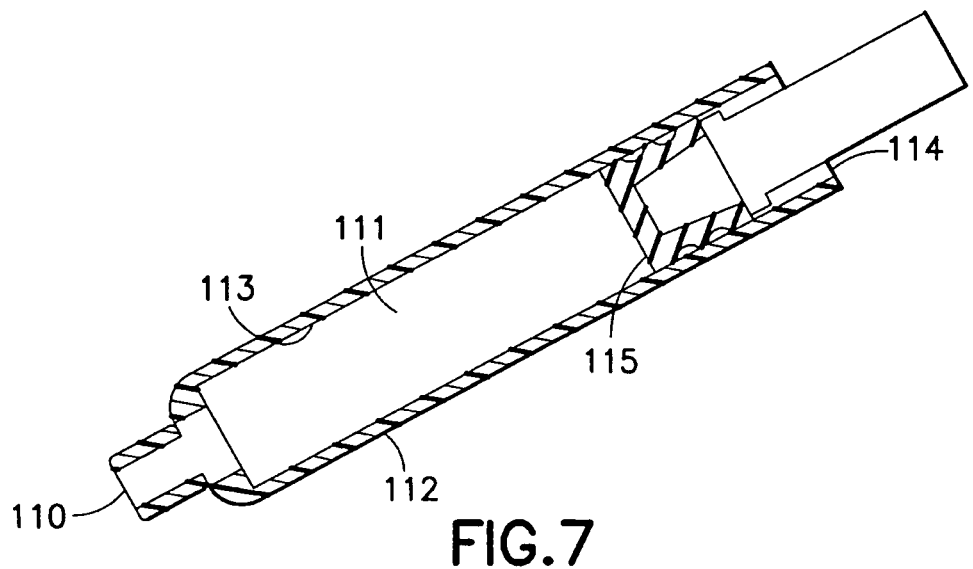
FIG. 7 is a perspective view in cross section of a stopper according to an exemplary embodiment of the present invention disposed within a cartridge of the drug delivery pen of FIGS. 1 and 2.
Figure 13:
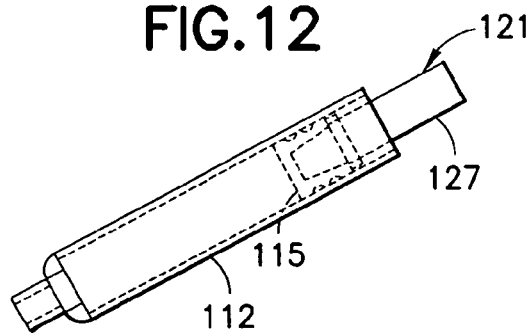
FIG. 13 is an elevational view of the stopper and driving member of FIGS. 11 and 12 disposed in a cartridge.

As shown in FIGS. 7, 10, 13 and 28-30, the driving member 121 has a first end 126 and a second end 128. As shown in FIGS. 7 and 13, the first end 126 of the driving member 121 is disposed in the cartridge 112 and the second end 128 is disposed outside of the cartridge. The driving member 121 includes a drive screw 127 with a spinner 123 connected thereto. As shown in FIG. 29, the drive screw 127 has a pin mating at a location 129 inside the spinner 123, thereby allowing the spinner to freely rotate.

A stopper 115 has a substantially frusto-conically shaped cavity 117, as shown in FIGS. 6, 7, 9, 11-14, 19 and 28-31. The plunger or driving member 121 has a mating substantially frusto-conically shaped spinner 123 with a flange 125 that substantially corresponds to the stopper cavity 117.

Figure 8:
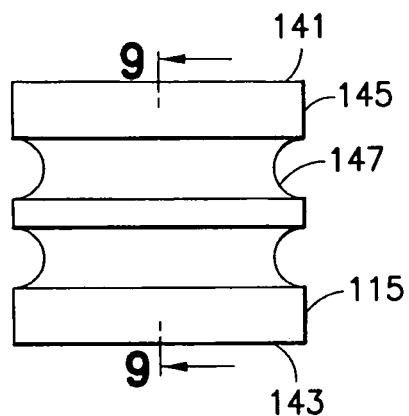
FIG. 8 is an elevational view of the stopper of FIG. 7.
Figure 9:
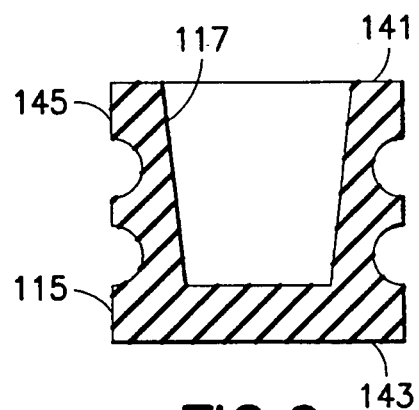
FIG. 9 is an elevational view of the stopper of FIG. 8 taken along line 9-9.
Figure 10:
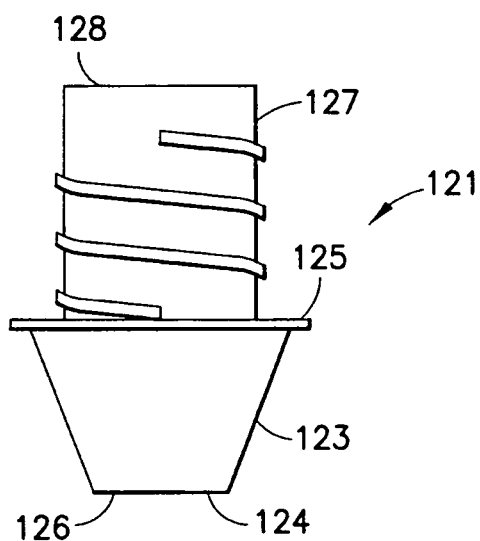
FIG. 10 is an elevational view of the driving member according to an exemplary embodiment of the present invention.
Figure 11:
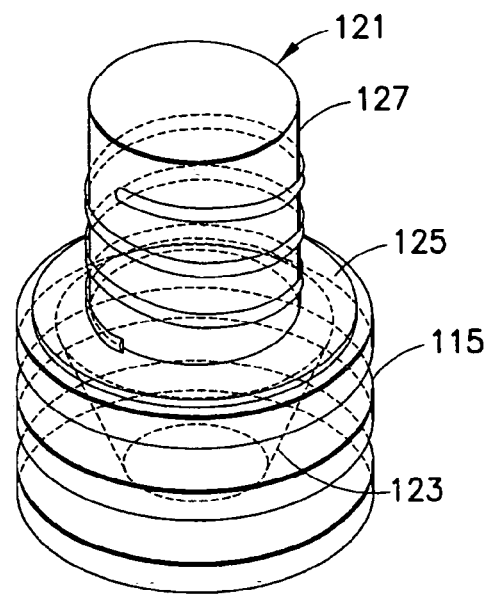
FIGS. 11 and 12 are perspective and elevational views, respectively, of the stopper and driving member according to an exemplary embodiment of the present invention.
Figure 12:
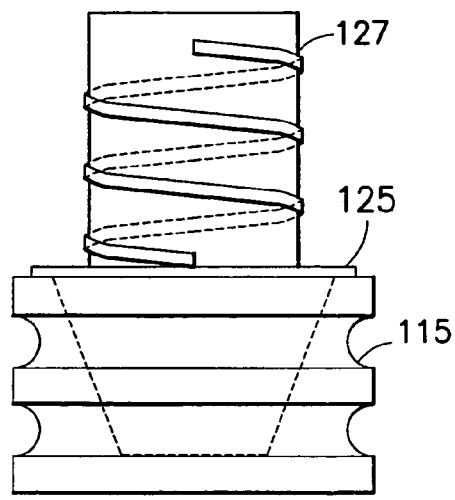
Figure 14:
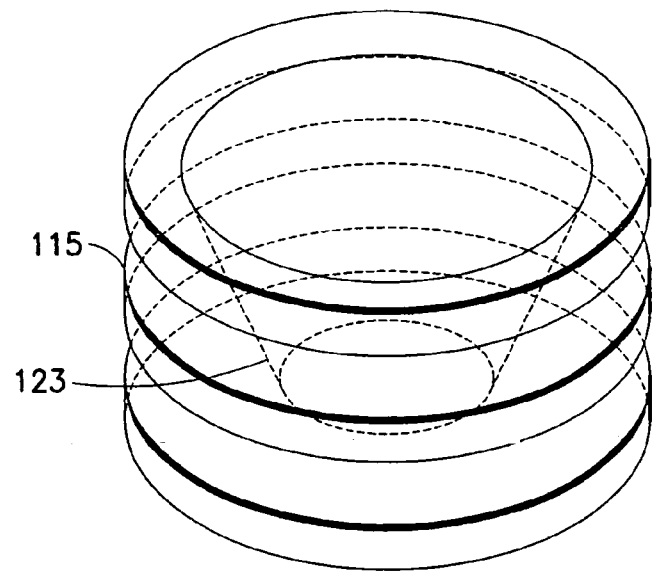
FIG. 14 is a perspective view of a stopper having a tapered cavity.
Figure 15:
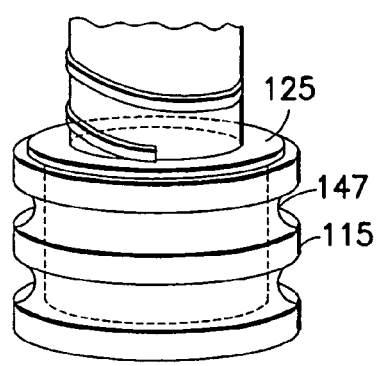
FIG. 15 is a perspective view of the stopper and driving member according to an exemplary embodiment of the present invention.
Figure 16:
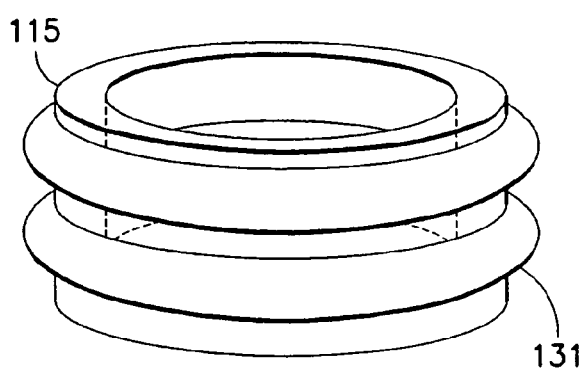
FIG. 16 is a perspective view of the stopper having O-rings disposed on an outer surface thereof.
Figure 17:
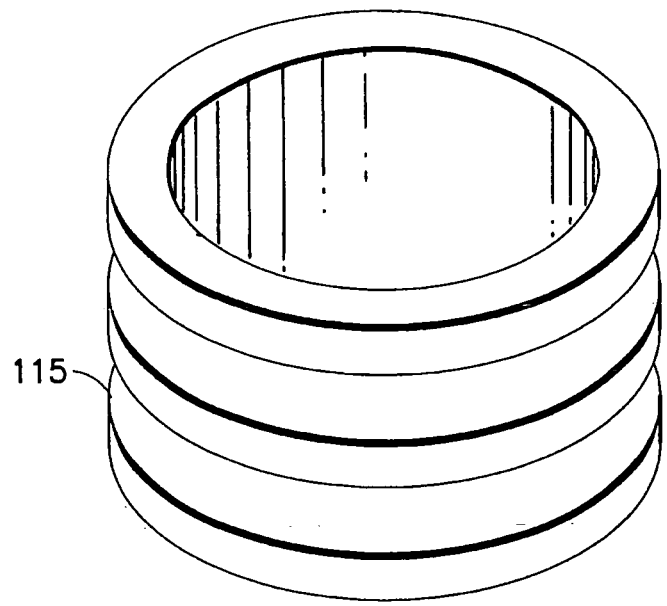
FIGS. 17 and 18 are perspective and cross-sectional views, respectively, of a stopper having a substantially cylindrical cavity.
Figure 18:
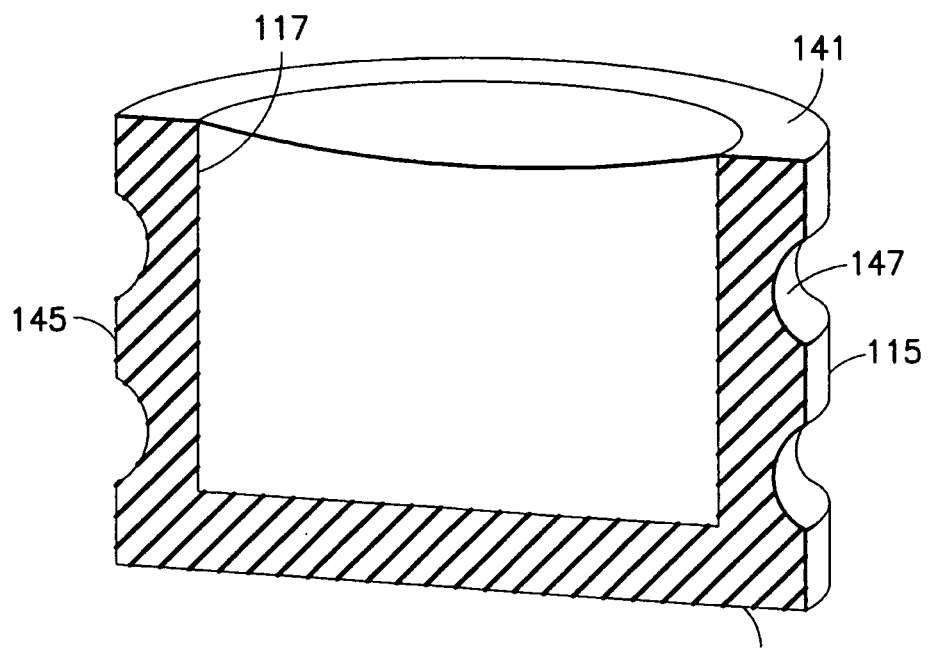
Figure 19:
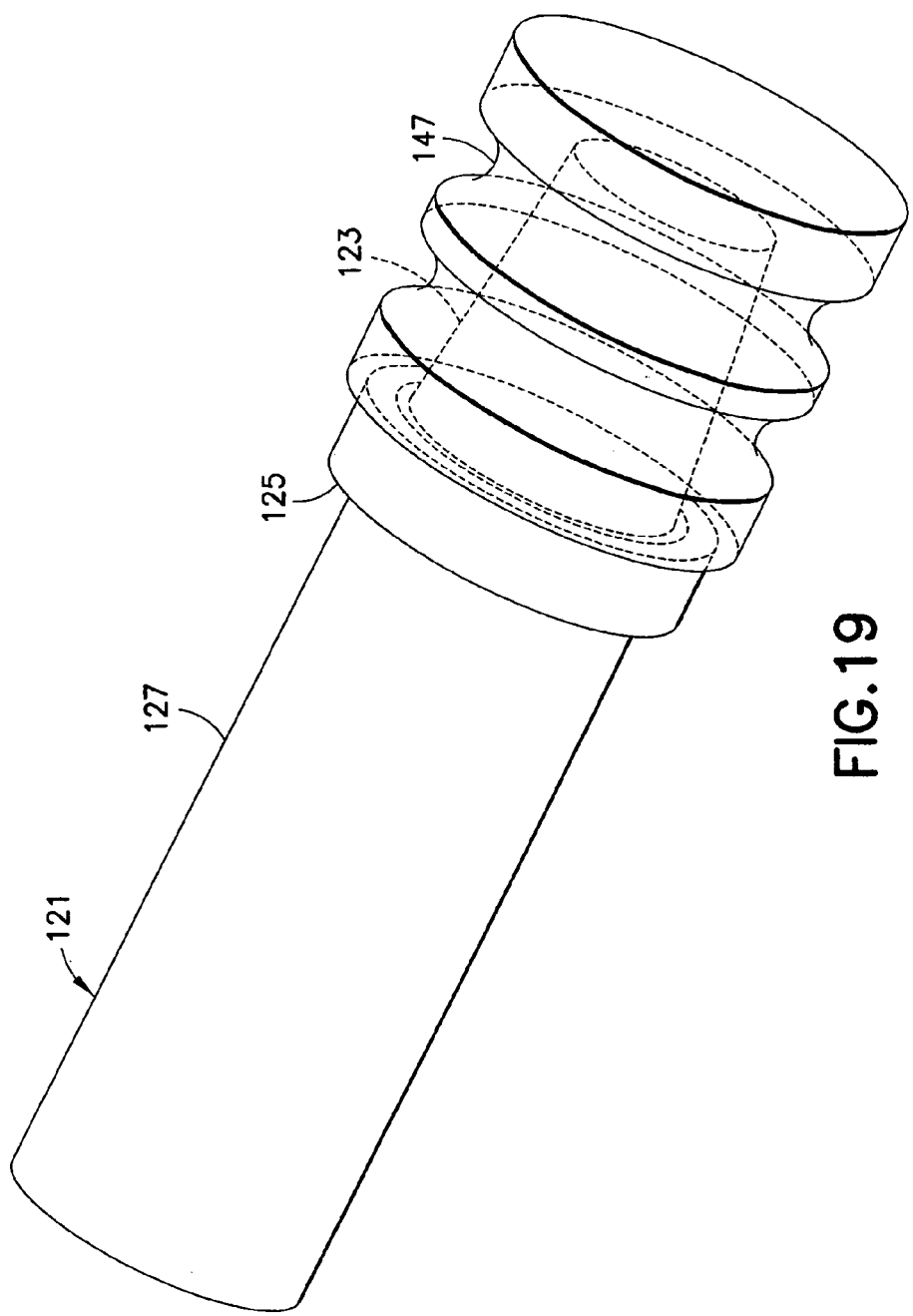
FIG. 19 is a perspective view of the stopper and driving member according to an exemplary embodiment of the present invention.
Figure 20:
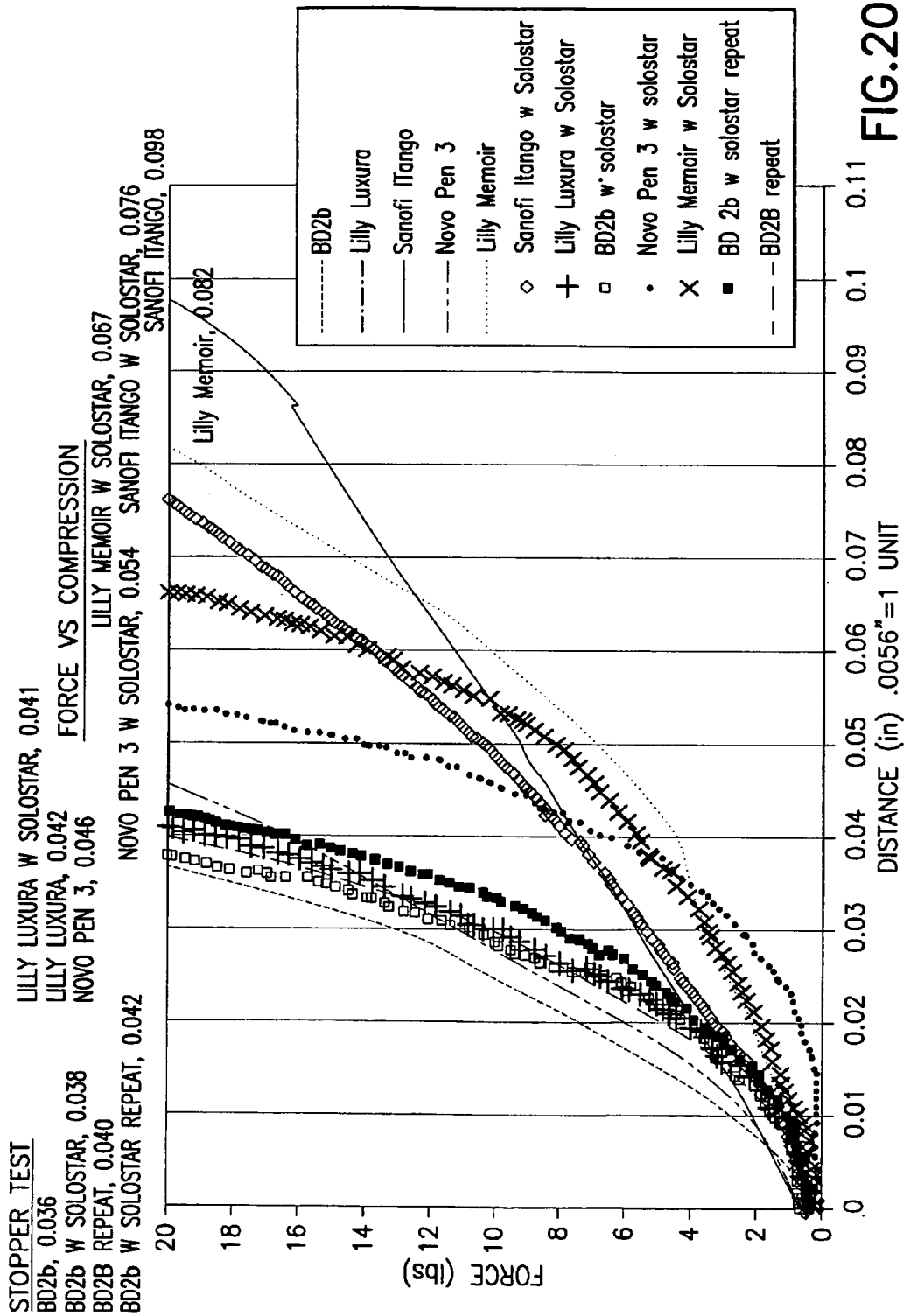
FIG. 20 is a graph of compression caused by force in various delivery devices.
Figure 21:
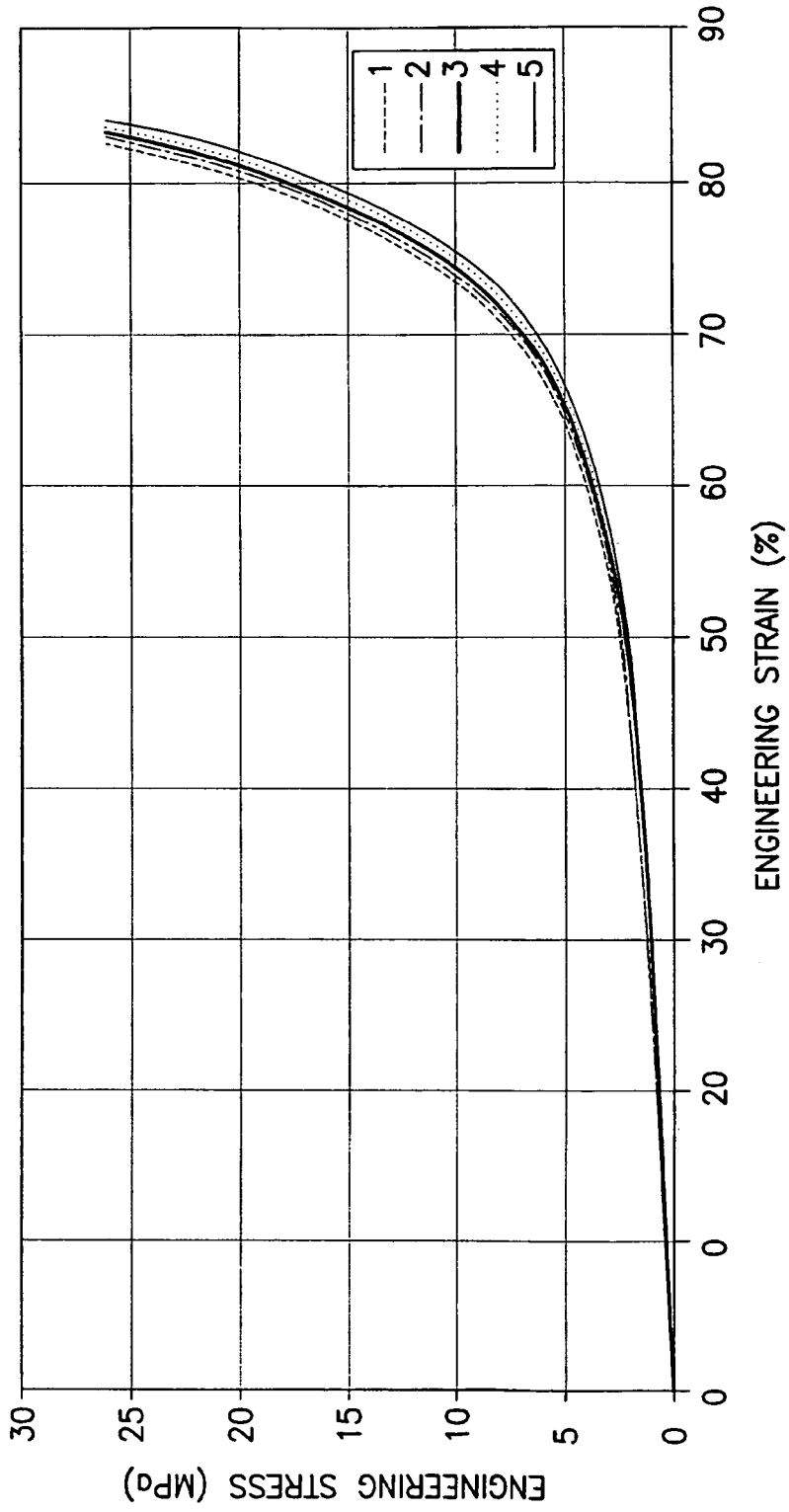
FIG. 21 is a stress-strain curve for a stopper material used in a drug therapy cartridge, such as insulin cartridge for various delivery devices.

As shown in FIGS. 8 and 9, the stopper 115 has a first end 141 and a second end 143. The stopper is slidably (axially) disposed in the cartridge 112, as shown in FIGS. 7, 13, 28 and 29. An outer surface 145 of the stopper 115 abuts the inner surface 113 of the cartridge 112. The cavity 117 is accessed through the first end 141 of the stopper 115. A recess 147 may be formed in the outer surface 145 of the stopper 115 to receive an O-ring 131 (FIG. 16). The cavity 117 may have a substantially frusto-conical shape as shown in FIGS. 9 and 14, a substantially cylindrical shape as shown in FIGS. 15, 17 and 18, or any other suitable shape.

Figure 30:
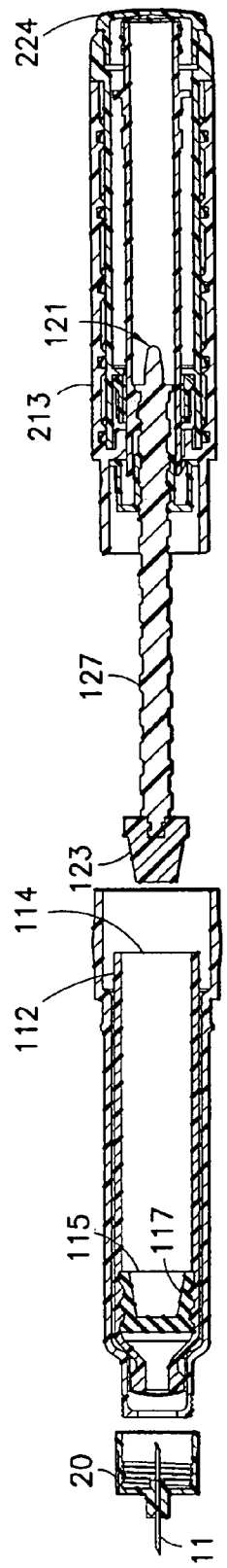
FIG. 30 is an elevational view in cross section of the drug delivery pen of FIG. 29 in which the needle hub, cartridge and outer sleeve are separated.

FIGS. 28-30 are elevational views in cross section of a drug delivery 200 including a stopper 115 and driving member 121 according to an exemplary embodiment of the present invention. The dose knob/button 224 has a dual purpose and is used to both set the dosage of the medication to be injected and used to inject the dosed medicament via the driving member 121 and stopper 115 through the medicament cartridge 112 and through the hub or reservoir housing (FIG. 2). The distal movement of the stopper 115 within the medicament cartridge 112 causes medication to be forced into the reservoir housing 20. The medicament cartridge 12 is sealed by septum 16, which is punctured by a septum penetrating needle cannula 11 located within reservoir housing. Reservoir housing 20 is preferably screwed onto the medicament cartridge 112, although other attachment means can be used. The cap 221 fits snugly against outer sleeve 213 to allow a user to securely carry the drug delivery pen 200.

As doses of the medicament are administered, the drive screw 127 moves the stopper 115 axially in the cartridge 112 toward the first end 110 of the cartridge 112, as shown in FIGS. 28 and 29. Once the medicament stored in the cartridge volume 111 has been depleted or the cartridge is to be discarded, the drive screw 127 is moved axially in the direction of the second end 114 of the cartridge 112, thereby separating the spinner 123 from the stopper cavity 117, as shown in FIG. 30. When the spinner 123 and stopper 115 have been separated, the cartridge 112 and stopper 115 may be discarded in an appropriate manner.

Figure 6:
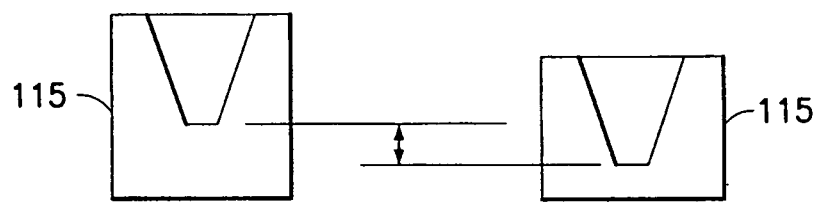
FIG. 6 is an illustration of the compression of a stopper according to an exemplary embodiment of the present invention.

The stopper 115 reduces deformation in cartridges, syringes and other equivalent delivery systems that encounter high pressures, such as back pressures, from intradermal injections, from the use of a thin needle gage, from the injection of viscous liquid, or from a high speed injection. The shape of the stopper 115 allows the driving member 121 to mate inside of the stopper 115, thereby giving the stopper support while at the same time allowing the driving member 121 to be "self-centering" because of the tapered walls. By reducing the height (thickness) of the soft rubber of the stopper 115 disposed in the cartridge 112 and replacing it with the rigid plastic spinner 123 of the driving member 121, the volume compression is reduced without changing materials, as shown in FIG. 6. Thus, the stopper 115 may be made of currently approved stopper materials that are validated for long-term insulin contact. The shape of the stopper changes driving of the stopper from "pushing" to "pulling" as illustrated in FIGS. 5 and 6, thereby minimizing the volume of the material compressed.

The shape of the stopper increases the effective hardness of the stopper 115 by utilizing a mating spinner 123 as the hard core component. Therefore, one advantage is that the volume compression under high pressure is reduced, as shown in FIG. 6, thereby increasing delivery dose accuracy, which is important for insulin or other dosage critical drug delivery. By maintaining the overall part count, a good economic benefit is provided.

The spinner 123 is substantially frusto-conically shaped to provide a "self-centering" function when mated with the stopper cavity 117. This ensures axial alignment of the stopper 115 and driving member 121. The spinner 123 has a wider base proximal the drive screw 127 than at the free end 124, thereby facilitating removal of the spinner from the stopper 115. Also, a flange 125 may be disposed between the spinner 123 and the drive screw 127 to increase the contact area with the stopper 115 to further reduce the stopper deformation under high pressure. The rigid inner spinner 123 prevents the stopper 115 from collapsing under high pressure. Furthermore, the cartridge 112 to stopper 115 surface contact for proper sealing is maintained.

In another exemplary embodiment of the present invention the stopper has a cavity wall that is substantially straight (i.e., a cylindrically shaped cavity) and a mating plunger spinner that is substantially cylindrical, as shown in FIGS. 15, 17 and 18. In another exemplary embodiment, the driving member 121 does not have a flange.

In still another exemplary embodiment shown in FIG. 16, a rigid stopper has a semi-rigid or flexible O-ring 131 disposed on an outer surface 145 of the stopper 115 to further increase the effective hardness of the stopper, thereby reducing the compressibility of the stopper. The O-ring 131 also enhances the sealing property of the stopper 115 so that the overall height of the stopper may be reduced without compromising sealing capability. By reducing the overall height of the stopper 115, the volume compression of the stopper is further reduced, thereby improving the dose accuracy.

Figure 31:
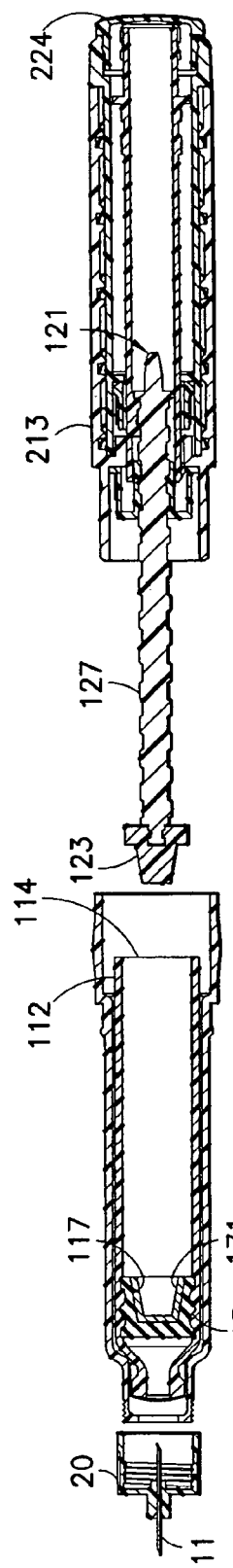
FIG. 31 is an elevational view in cross section of the drug delivery pen of FIG. 30 in which the stopper has an insert.

In another exemplary embodiment, a harder material insert 171 is disposed inside the stopper 115 in the cavity 117 but not enclosed in the outer softer material, as shown in FIG. 31. The outer material of the stopper 115 is softer for proper sealing. The inside second harder material of the insert 171 has a corresponding surface to mate with the spinner 123 of the driving member 121. This second material may be almost incompressible. The stopper of FIG. 17 reduces the effective compressibility and, therefore, increases dose accuracy.

TABLE I

| Volume (unit) | 200 psi | 100 psi | 50 psi | 25 psi | 10 psi |
|---|---|---|---|---|---|
| Existing Stopper Design | 10.5 | 6.5 | 3.7 | 1.7 | 0.7 |
| Stopper According to Exemplary Embodiment | 2.7 | 1.6 | 1 | 0.5 | 0.2 |

The initial breakout pressure may be as high as 200 psi, or higher in some applications, and the typical equilibrium pressure is between approximately 30-50 psi. As shown in Table I, one unit of dose accuracy is achieved with a stopper according to an exemplary embodiment of the present invention. The existing stopper design, as shown in FIGS. 3 and 4, does not meet application dose accuracy requirements, as shown in Table I. Furthermore, Table I indicates the improved dose accuracy between the existing stopper and the stopper according to an exemplary embodiment of the present invention.

Figure 22:
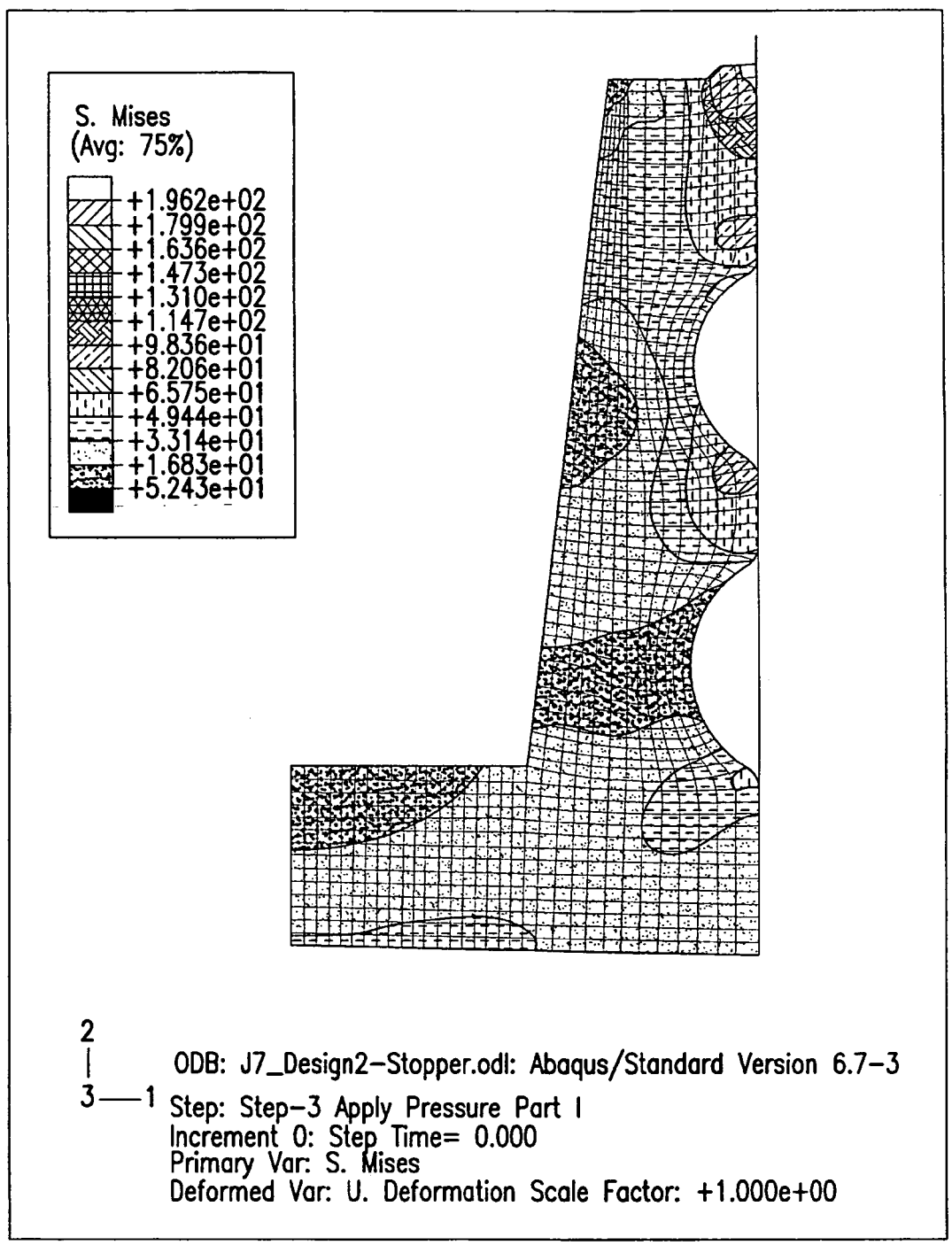
FIGS. 22 and 23 are finite element analysis graphs before and after the application of pressure to a stopper according to an exemplary embodiment of the present invention.
Figure 23:
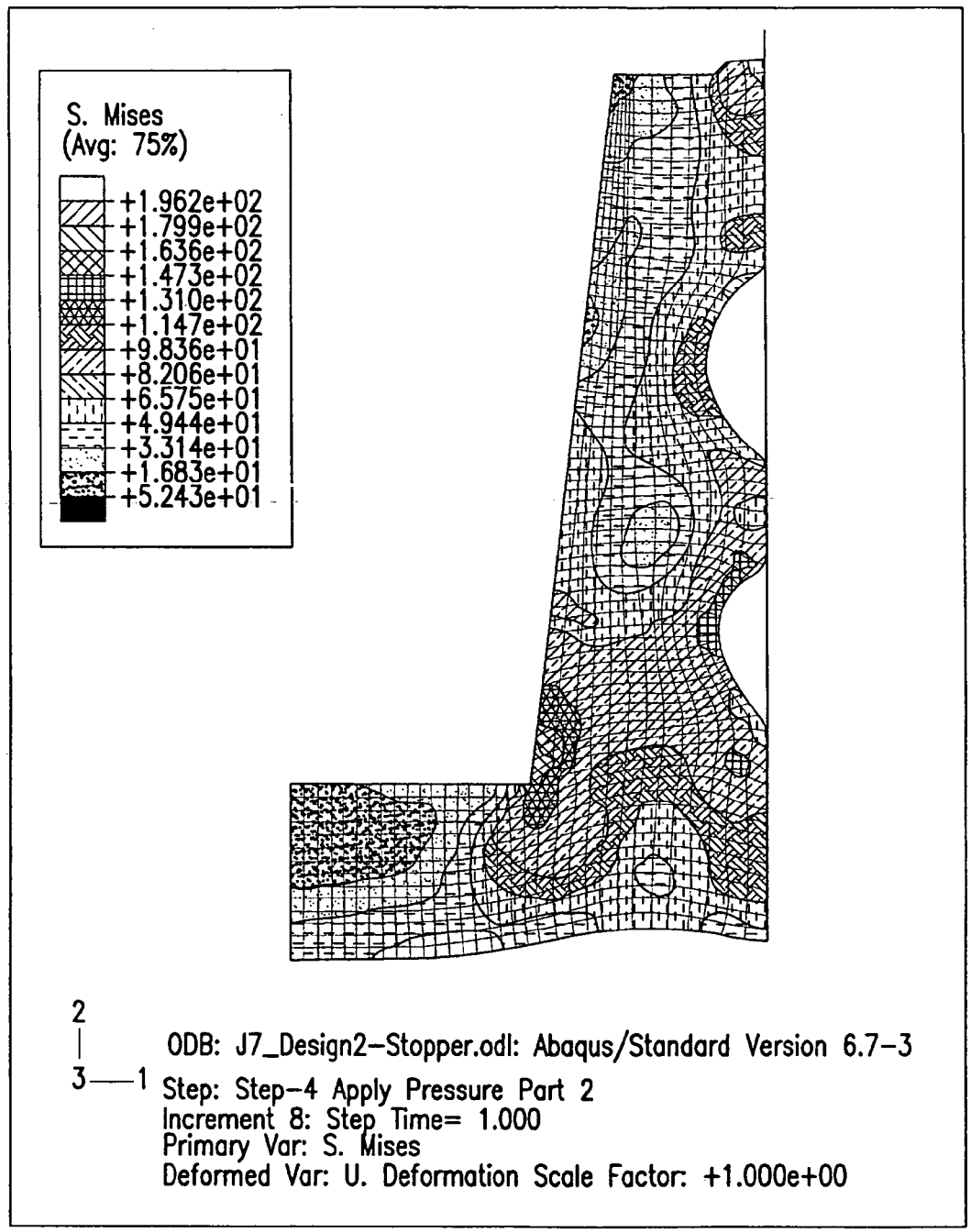
Figure 24:
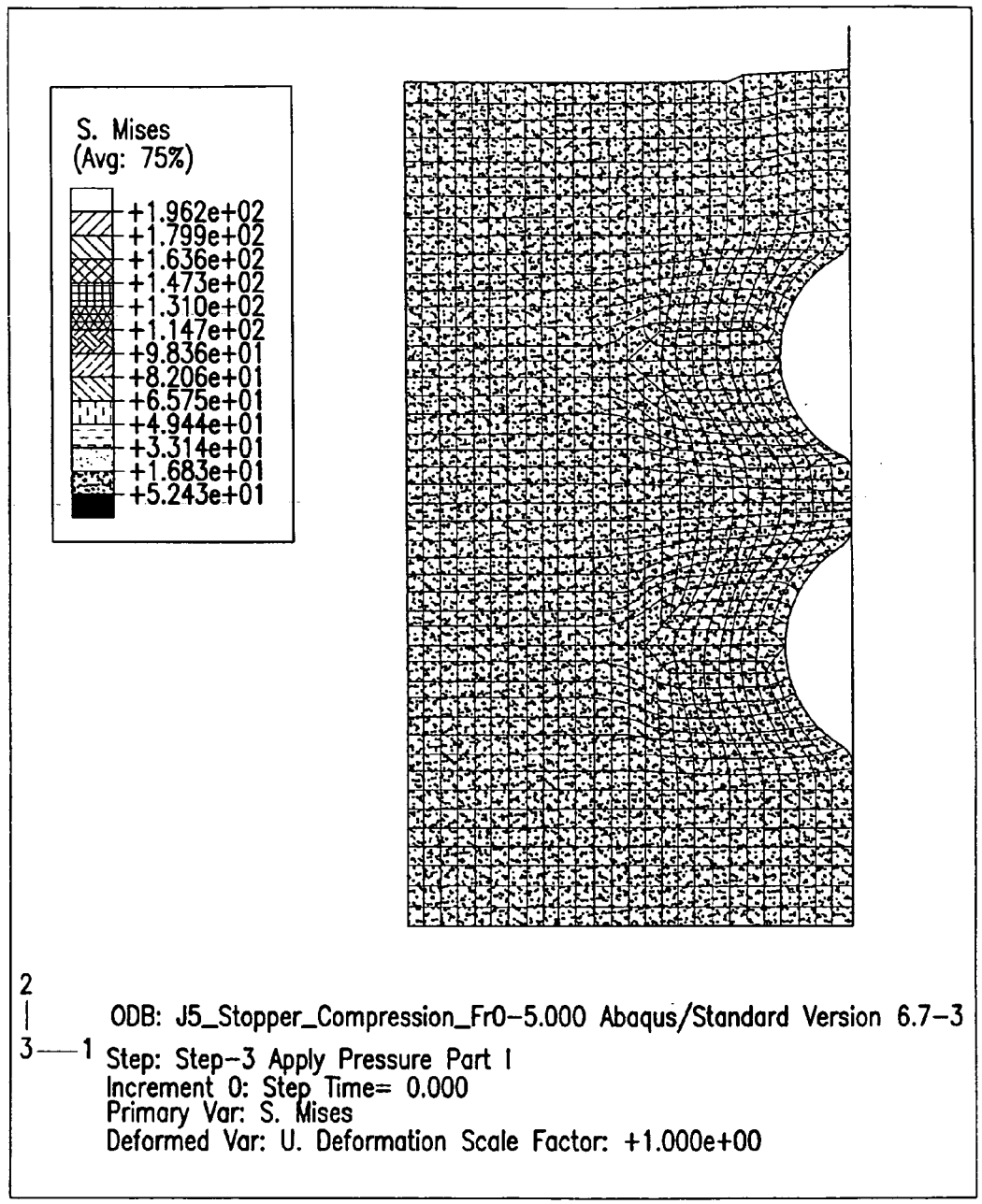
FIGS. 24 and 25 are finite element analysis graphs before and after the application of pressure to an existing stopper.
Figure 25:
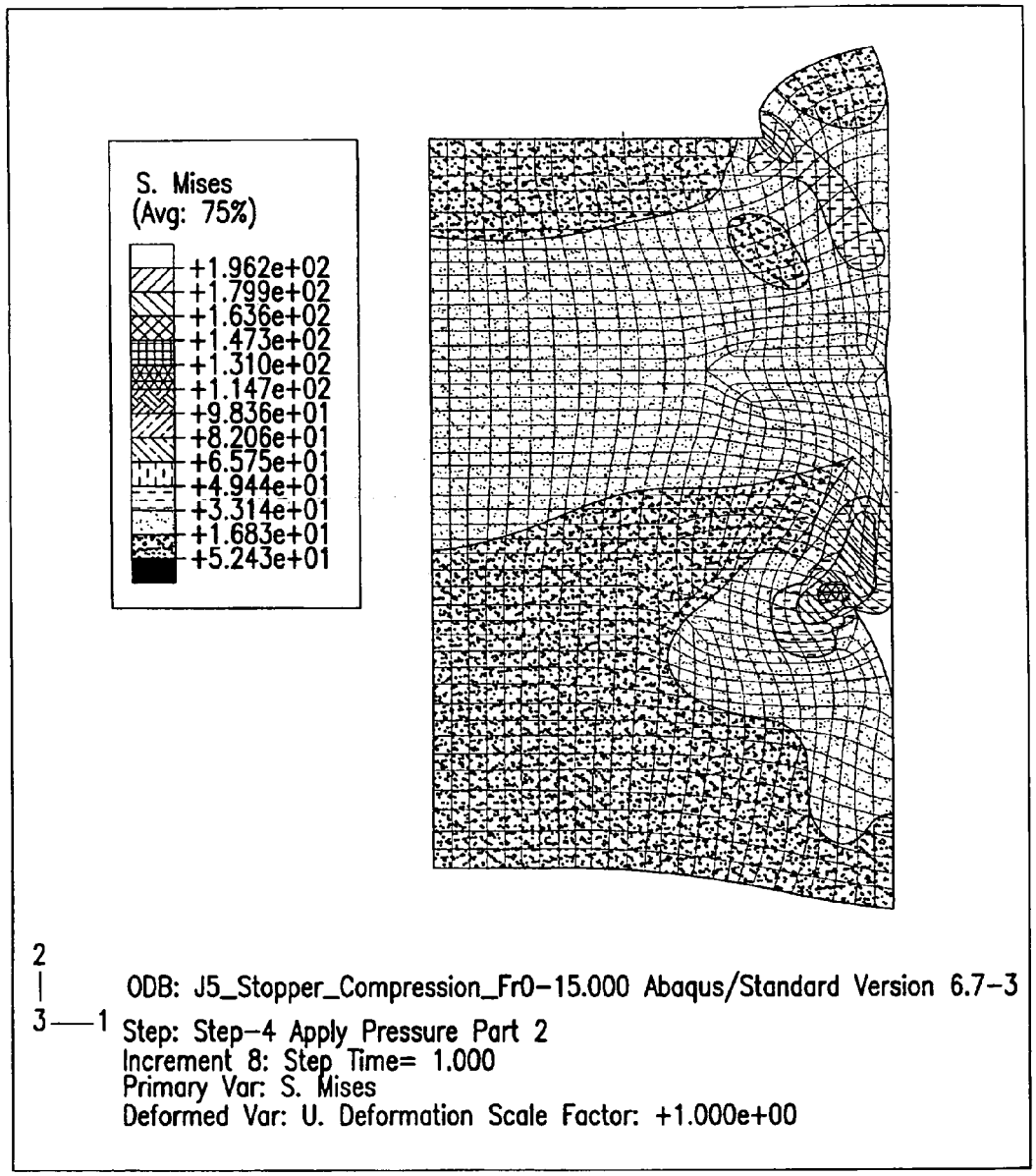
Figure 26:
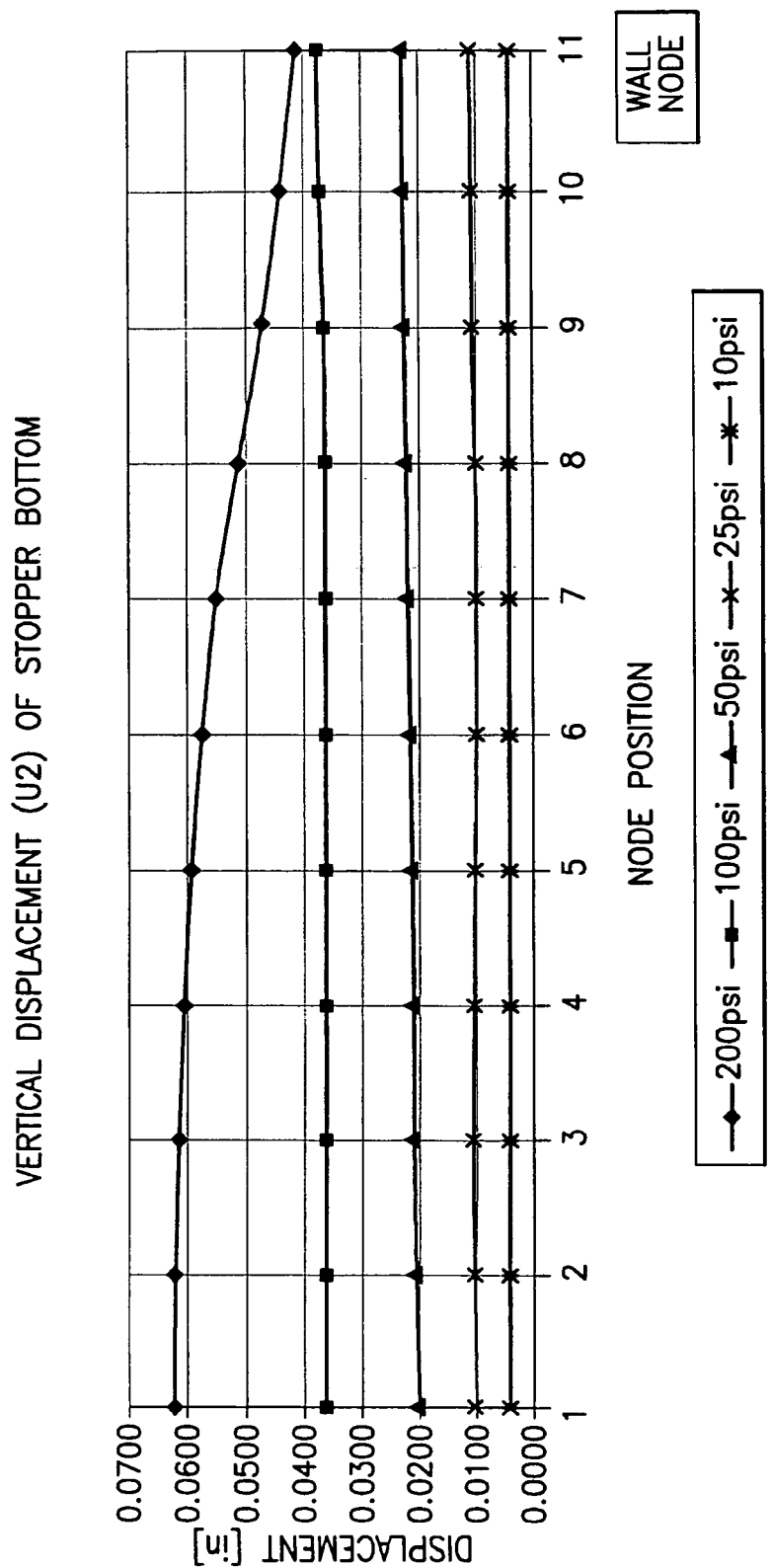
FIG. 26 is a graph of the vertical displacement of the stopper bottom for an existing stopper.
Figure 27:
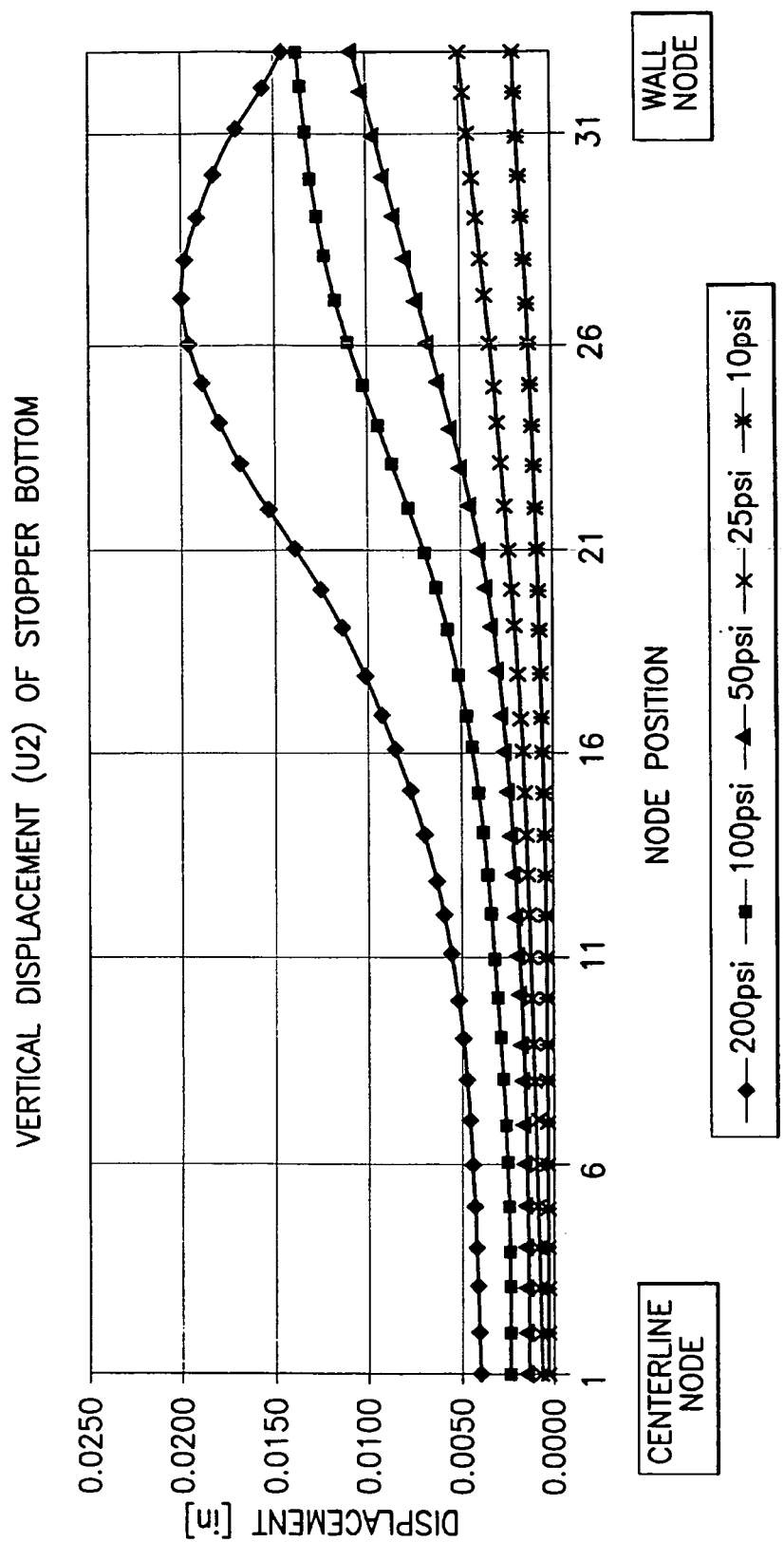
FIG. 27 is a graph of the vertical displacement of the stopper bottom for a stopper according to an exemplary embodiment of the present invention.

Results of finite element analyses of a stopper according to an exemplary embodiment of the present invention are shown in FIGS. 22 and 23 and an existing stopper in FIGS. 24 and 25. FIGS. 22 and 24 show the stoppers prior to application of pressure and FIGS. 23 and 25 show the stoppers after the application of pressure. As clearly shown in FIGS. 23 and 25, a stopper according to an exemplary embodiment of the present invention deformed significantly less than an existing stopper.

While exemplary embodiments have been chosen to illustrate the invention, it will be understood by those skilled in the art that various changes and modifications may be made therein without departing from the scope of the invention as defined in the appended claims.

The invention claimed is:

1. A device for delivering a medicament, comprising:
   a cartridge having a first end and a second end and defining a volume therebetween, said volume being adapted to contain the medicament;
   a driving member having a mating pin and a first end and a second end, said first end being disposed in said cartridge and said second end being disposed outside said cartridge;
   a spinner directly engaged to said first end of said driving member via said mating pin disposed inside said spinner to secure said spinner to said driving member and allow free rotation between said spinner and said driving member; and
   a stopper having a substantially frusto-conically shaped cavity mating with said spinner, said stopper slidably disposed in said cartridge volume, said spinner being releasably connected to said stopper such that when said driving member is retracted from said cartridge said stopper is disengaged from said spinner and remains in said cartridge volume.

2. The device of claim 1, wherein
   at least one O-ring is disposed between an outer surface of said stopper and an inner surface of said cartridge.

3. The device of claim 2, wherein
   a groove is formed in said outer surface of said stopper to receive said at least one O-ring.

4. The device of claim 1, wherein
   a flange is disposed on said spinner and abuts an end of said stopper.

5. The device of claim 1, wherein
   said spinner is substantially frusto-conically shaped.

6. The device of claim 5, wherein
   said stopper is made of a rubber material and said spinner is made of a plastic material.

7. The device of claim 5, wherein
   said spinner is connected to a drive screw of said driving member, and said spinner has a wider base proximal of the drive screw than at a free end of said spinner.

8. The device of claim 7, wherein
   a flange is disposed between said spinner and said drive screw of said driving member, and said flange being wider than said stopper cavity.

9. The device of claim 1, wherein
   said spinner is substantially cylindrically shaped and is releasably disposed in said stopper cavity.

10. The device of claim 1, wherein
    a first portion of said stopper contacts an inner surface of said cartridge and a second portion of said stopper contacts said spinner, and said first portion is made of a softer material than said second portion.

11. An apparatus for use in a device for delivering a medicament, comprising:
- a rotating driving member having a mating pin and a first end and a second end;
- a stopper having a cavity in a first end; and
- a spinner received in said stopper cavity and directly engaged to said first end of said driving member via said mating pin disposed inside said spinner to secure said spinner to said driving member and resist rotation of said spinner with respect to said stopper during rotation of said driving member, said spinner being releasably connected to said stopper cavity, and said spinner having a flange that is wider than said stopper cavity and that abuts said first end of said stopper.

12. The device of claim 11, wherein
said stopper cavity is substantially frusto-conically shaped.

13. The device of claim 12, wherein
said spinner is substantially frusto-conically shaped.

14. The device of claim 11, wherein
said stopper is made of a rubber material and said spinner is made of a plastic material.

15. The device of claim 11, wherein
said cavity is substantially cylindrically shaped; and
said spinner is substantially cylindrically shaped.

16. The device of claim 11, wherein
a second portion of said stopper contacts said spinner of said driving member, and a first portion of said stopper surrounding said second portion is made of a softer material than said second portion.

17. A device for delivering a medicament, comprising:
- a cartridge having a first end and a second end and defining a volume therebetween;
- an outer sleeve connected to said cartridge;
- a dose set knob connected to said outer sleeve;
- a driving member having a mating pin and a first end, a second end, and a drive thread rotatably coupling said driving member to said dose set knob;
- a stopper having a substantially frusto-conically shaped cavity mating with a spinner, said stopper slidably disposed in said cartridge; and
- said spinner directly engaged to said first end of said driving member via said mating pin disposed inside said spinner to secure said spinner to said driving member and allow free rotation between said spinner and said driving member, said spinner being releasably connected to said stopper such that when said driving member is retracted from said cartridge said stopper is disengaged from said spinner.

* * * * *